United States Patent [19]

Bianco et al.

[11] Patent Number: 5,387,239
[45] Date of Patent: Feb. 7, 1995

[54] ADJUSTABLE LENGTH PROSTHETIC IMPLANT

[75] Inventors: Peter T. Bianco, Newton, Mass.; Roy S. Boggan, Cordova, Tenn.

[73] Assignee: Wright Medical Technology, Inc., Arlington, Tenn.

[21] Appl. No.: 49,756

[22] Filed: Apr. 19, 1993

[51] Int. Cl.⁶ .............................. A61F 2/30
[52] U.S. Cl. ........................ 623/18; 623/38; 606/63; 403/118; 411/246; 411/265; 411/433; 411/436
[58] Field of Search ............ 606/63, 73; 623/38, 623/18, 20; 403/46, 118; 411/246, 247, 265, 270, 423, 433, 436

[56] References Cited

U.S. PATENT DOCUMENTS

| | | | |
|---|---|---|---|
| 4,023,914 | 5/1977 | Holmes | 411/436 X |
| 4,171,012 | 10/1979 | Holmes | 411/436 X |
| 4,549,754 | 10/1985 | Saunders et al. | 411/423 X |
| 5,282,707 | 2/1994 | Palm | 411/3 |
| 5,326,360 | 7/1994 | Kotz et al. | 623/20 |

FOREIGN PATENT DOCUMENTS 0065344 11/1982 European Pat. Off.
0212192 10/1987 European Pat. Off.
0295718 4/1932 Italy .................................. 403/46
0194042 1/1965 Sweden .

OTHER PUBLICATIONS

Detroit Tool Industries, "Spiralock ™", Catalog No. 86-1, 2.5M–Mar. 1991.

*Primary Examiner*—David H. Willse

[57] ABSTRACT

An adjustable length prosthetic implant includes an implant body and an axially received stem. The stem has a threaded portion and an end portion adapted for mounting with a bone. The implant body includes an end portion adapted for mounting with a bone and a tubular sleeve. The sleeve adjustably receives the stem. An adjustment nut is rotatably carried upon the sleeve for threadably engaging the stem to effect telescopic length adjustment of the stem relative to the sleeve. A jam nut is threaded over the stem and forcibly tightened against the adjustment collar to prevent accidental adjustment of the stem. The female thread formation in each of the adjustment collar and jam nut includes a wedge ramp positioned across the thread root for engaging the thread crest of the corresponding male screw formation on the stem to evenly distribute stresses through the screw formations.

7 Claims, 2 Drawing Sheets

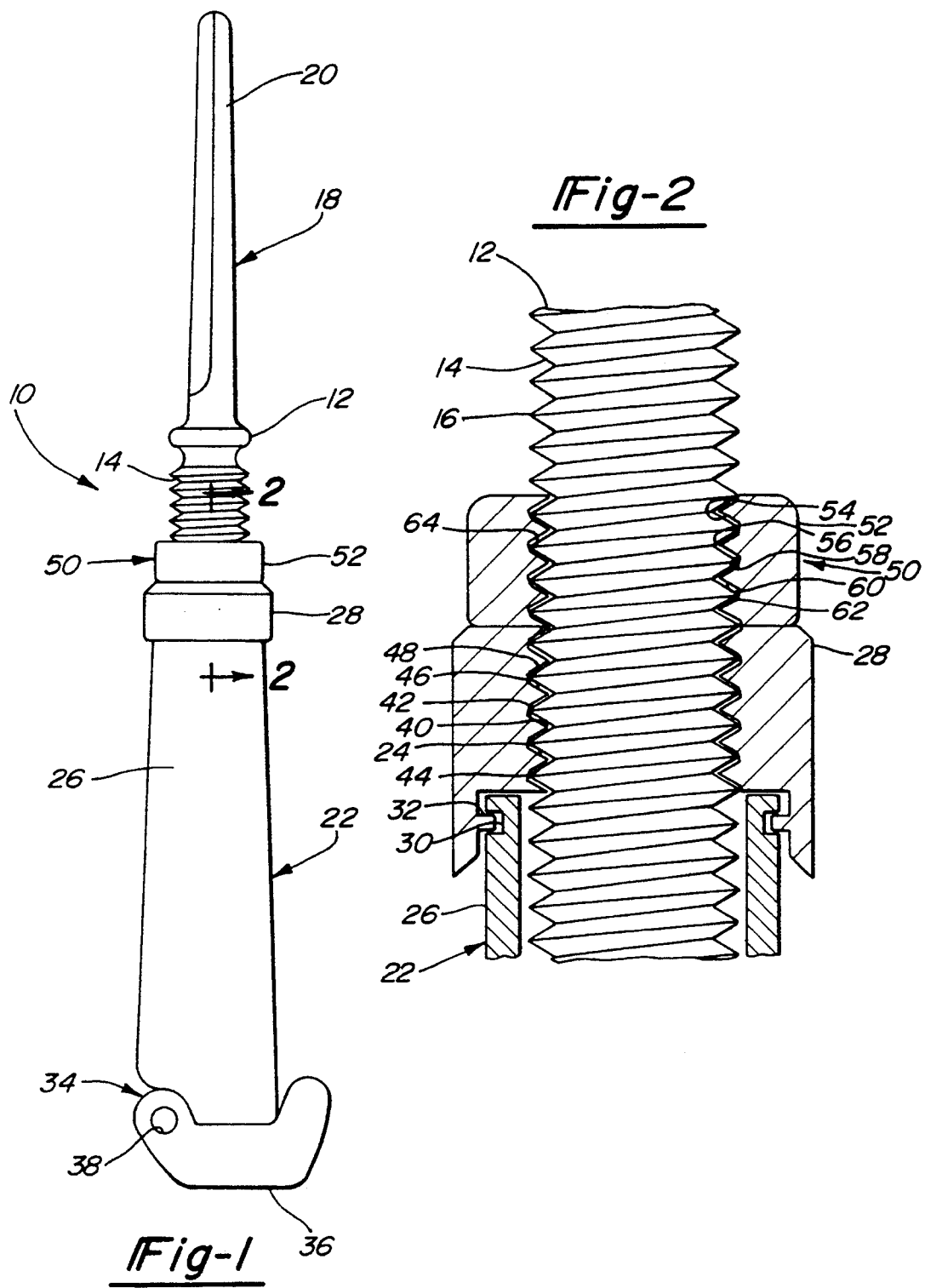

_5,387,239_

ADJUSTABLE LENGTH PROSTHETIC IMPLANT

TECHNICAL FIELD

The present invention relates to a surgically implantable prosthesis, and more particularly to a prosthesis suitable for juvenile patients which provides for length adjustment as the patient grows.

BACKGROUND OF THE INVENTION

Many types of skeletal implants and skeletal joint prosthesis are available for substitutes of natural skeletal components and joints. Such prostheses are used when the natural skeletal component has been damaged by disease or trauma. However, a problem exists in the case of juvenile patient's or other patients where natural growth would otherwise be occurring. As the patient grows, the limb having the prosthesis implanted will not grow at the same rate as the opposing limb unless the prosthesis allows for growth along its length.

The U.S. Pat. No. 4,892,546 to Kotz et al, issued Jan. 9, 1990, discloses an adjustable prosthesis for a bone joint including a joint component, an elongated rod having a distal end and a proximal end, a drive trunion connected to the rod through an annular gear, an elongated inner sleeve and an outer sleeve, and means for preventing rotation of the inner sleeve within the outer sleeve. The elongated rod includes a threaded spindle on the inner sleeve and a spindle nut which cooperates with the threaded spindle to provide extension and retraction adjustment of the rod relative to the inner sleeve.

The European Patent Application EP 86109228, assigned to Waldemar Link GmbH, discloses an endoprosthesis replacing bone middle sections including a tubular spacer with a collar at each end in a solid bone nail extending from one collar. A sliding nail fits in a bore of the tubular spacer and can be locked in any required position by a lock screw.

A joint implant is disclosed in the U.S. Pat. No. 4,502,160 to Moore et al., issued Mar. 5, 1985, and assigned to the assignee of the present invention, the disclosure of which is hereby incorporated by reference and relied upon. The Moore et al. patent discloses an implant including a stem for bone implantation including a threaded portion for adjusting axially with respect to an overlying sleeve which carries an articulating component of the joint. A pin in the sleeve and an elongated slot in the stem restrain relative rotation to allow axial relative movement as the stem is urged into or out of the sleeve by rotation of a nut coacting with the threads of the stem while being axially restrained by the sleeve. The nut acts as a ring gear.

Although the Moore et al. patent discloses a very useful embodiment for a prosthetic implant, it is possible that galling of the threads of the stem may occur caused by the significant structural forces placed on the threaded members during excessive physical activity of the patient. The possibility for galling of the threads is aggravated by the relatively soft biocompatible materials required in prosthetic implant appliances.

Catalog No. 86-1 entitled "Spiralock ™", distributed by Detroit Tool Industries, 25219 Dequindre Road, P.O. Box 71629, Madison Heights, Mich. 48071-0629, discloses a thread forming female tap which produces a wedge ramp along the root portion of the female thread form. The entire disclosure of this Spiralock ™ catalog is hereby incorporated by reference and relied upon. Specifically, the thread form produced by the Spiralock ™ tap incorporates a unique 30° wedge ramp which, at the point clamp loading is applied, contacts the crest of the corresponding male thread creating a continuous spiral contact along the entire length of the thread engagement. This has the effect of spreading the clamp force evenly along all of the threads, thereby reducing the undesirable occurrence of galling and premature component failure.

However, a Spiralock ™ thread form is not used in a typical jack screw, i.e., power screw, type arrangements since clamping loads necessary to activate the wedge ramp are not consistently encountered. Particularly in prosthetic implants, such as Moore et al., the intermittent loading encountered during normal human activities, such as walking, would yield the Spiralock ™.

The present invention provides an improvement over the implant disclosed in the Moore et al. patent by increasing the strength of the threaded components of the device while simultaneously decreasing the problem of galling.

SUMMARY OF THE INVENTION AND ADVANTAGES

In accordance with the present invention, there is provided an adjustable length prosthetic implant including an axially extending stem including a male screw having a helical thread crest. Stem fixation means is provided for mounting the stem to a bone. An implant body axially receives the stem and includes a female screw threadably engaging the male screw. The female screw has a helical wedge ramp for engaging the thread crest of the male screw. Body fixation means is provided for mounting the implant body to a bone at a location spaced from the stem fixation means. The improvement of the invention comprises locking means reactive between the implant body and the stem for forcibly maintaining the thread crest of the male screw in pressed contact with the wedge ramp to lock the stem in an axially adjusted position relative to the implant body while uniformly distributing stresses through the male screw and the female screw.

The locking means provides the necessary clamping force to continuously activate the wedge ramp contained in the female screw so that the advantages of the Spiralock ™ type thread form can be achieved. Thus, even during the intermittent loading encountered during normal human activities, the locking means maintains the crest of the male screw in forced engagement with the wedge ramp to take full advantage of the improved stress distribution through the threads and thereby help prevent galling.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a side elevation view of a preferred embodiment of the invention;

FIG. 2 is a simplified cross-sectional view taken along line 2—2 of FIG. 1; and

DESCRIPTION OF THE PREFERRED EMBODIMENT

Figure 3:
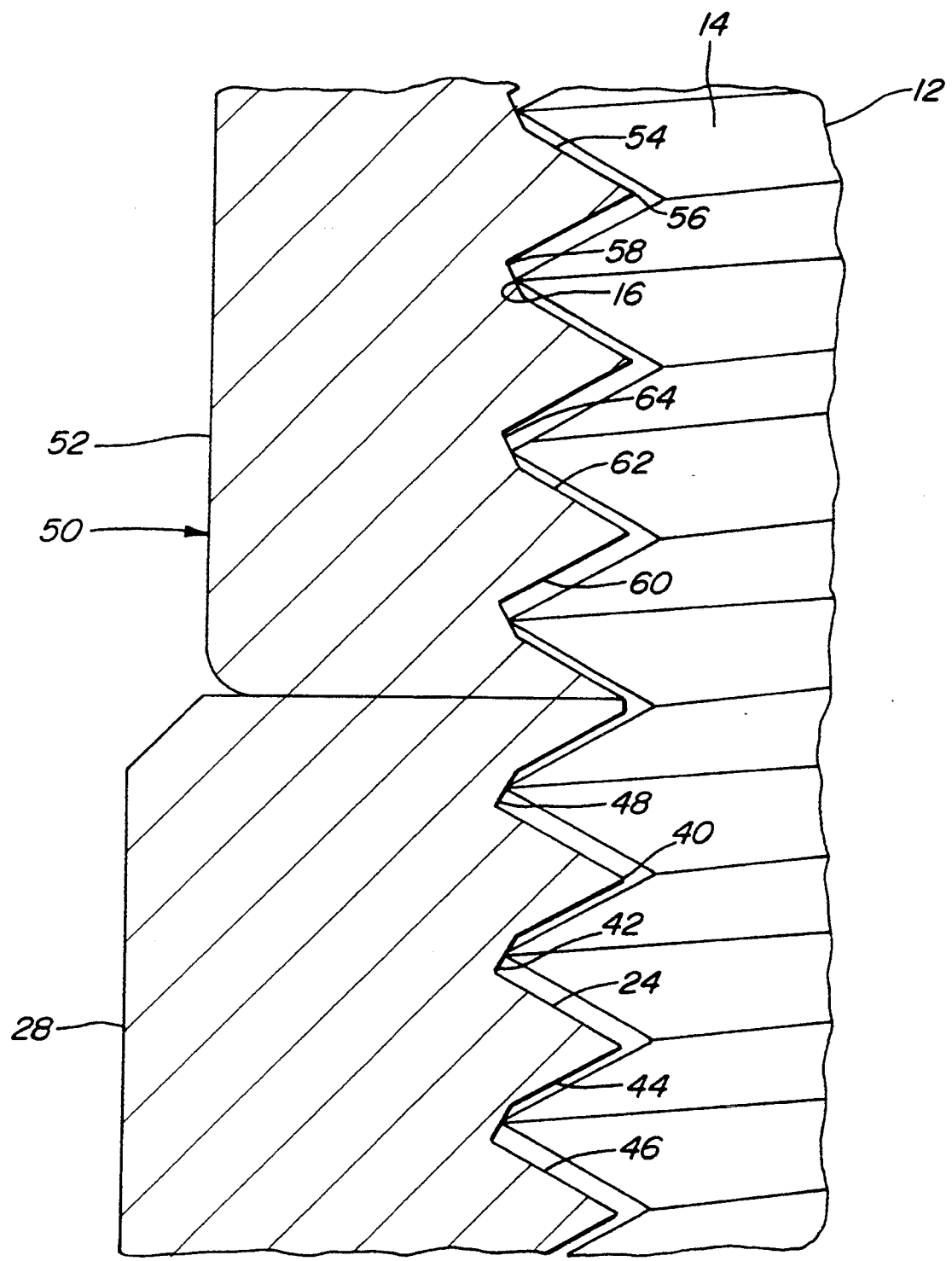
FIG. 3 is an enlarged cross-sectional view showing the interlocking male and female screw thread forms.

Referring to the drawings, wherein like reference numerals designate like or corresponding parts throughout the several views, an adjustable length prosthetic implant according to the subject invention is generally shown at 10 in FIG. 1. Although the invention shown in FIG. 1 takes the form of a femoral component of a surgically implantable prosthetic knee joint, the adjustable length prosthesis 10 may take many different forms, such as any other appropriate inter-bone or bone-joint replacement.

The prosthesis 10 includes an axially extending stem 12 having a male screw 14. In typical fashion, the thread form of the male screw 14 includes a helical thread crest 16 extending completely the length of the male screw 14.

A stem fixation means 18 is provided for mounting the stem 12 to a bone (not shown). In the embodiment illustrated in FIG. 1, the stem fixation means 18 comprises a taper portion 20 for either force-fit or cemented implantation in the intramedullary canal of the femur. In such an embodiment, the taper portion 20 is of non-circular cross-section to minimize the possibility of rotation after implantation. However, other adaptations of the implant 10 may dictate an alternation of the stem fixation means 18 to accommodate the given environment.

An implant body, generally indicated at 22, axially receives the stem 12. The implant body 22 includes a female screw 24 threadably engaging the male screw 14. Axial length adjustment of the stem 12 relative to the implant body 22 is effected by relative rotation between the female screw 24 and the male screw 14 in typical jack screw, or power screw, fashion. More particularly, the implant body 22 includes a tubular sleeve 26 and an adjustment collar 28 rotatably connected to the sleeve 26. As shown in FIG. 2, the exterior surface of the sleeve 26 may be provided with an annular groove 30 for receiving an annular flange 32 extending inwardly from the adjustment collar 28. Of course, other alternative arrangements for rotatably connecting the adjustment collar 28 to the sleeve 26 are possible, including a simple ball bearing configuration which would reduce the relative friction between the adjustment collar 28 and the sleeve 26.

Body fixation means, generally indicated at 34, is provided for mounting the implant body 22 at a location spaced from the stem fixation means 18. In the embodiment illustrated in FIG. 1, the body fixation means 34 is connected to the lower, or distal, end of the sleeve 26 and comprises an articulating component having condylar portions 36 designed to articulate with the patella and tibial components (not shown). In this configuration, a pair of aligned holes 38 are provided for insertion of a hinge pin which connects the femoral component to an upstanding post of the tibial component. In this manner, the femoral and tibial articulating surfaces may be of many conventional shapes so as to achieve appropriate fixation of the implant body 22 in the environment in which the subject invention 10 is installed. Thus, the body fixation means 34 may take the form of an articulating component for some other joined or another intramedullary implant, depending upon the application.

The female screw thread form 24 is disposed within the adjustment collar 28 and includes a helical thread crest 40 and a thread root 42 with an interposed leading flank 44 facing toward the body fixation means 34 and a trailing flank 46 facing away from the body fixation means 34. The female screw 24 includes a helical wedge ramp 48 for engaging the thread crest 16 of the male screw 14. The wedge ramp 48 is of the type marketed under the name Spiralock TM and includes a 30° wedge ramp disposed along the root 42. Specifically, the wedge ramp 48 is positioned across the root 42 and angles gradually and outwardly from the leading flank 44 toward the trailing flank 46. In this manner, the crest 16 of the male screw 14 engages and bears against only the wedge ramp 48 of the female screw 24 upon application of the clamping force.

Although not shown, the stem 12 and sleeve 26 may be provided with a structure for preventing relative rotation therebetween. For example, as shown in the Moore et al U.S. Pat. No. 4,502,160, a pin or key may extend through the sleeve into an elongated slot in the stem 12 to restrain relative rotation between the two members.

A primary contributor to the premature failure of screw components in the prior art results from the necessary running clearance between the male and female screw thread profiles. Without such a clearance, frictional forces would prevent smooth threaded engagement between the male and female screw thread forms. However, such running clearance inevitably leads to backlash, or lost motion, between the male and female screw thread forms. This backlash results in galling and, hence, premature failure of the implant components. However, according to the prior art, the running clearance between the male and female screw thread forms goes encountered as typical in jack screw of power screw arrangements.

In order to minimize the undesirable effects of galling fostered by the running clearance between the screw threads, the subject invention is provided with locking means, generally indicated at 50, reactive between the implant body 22 and the stem 12 for forcibly maintaining the thread crest 16 of the male screw 14 in pressed contact with the wedge ramp 48 to lock the stem 12 in an axially adjusted position relative to the implant body 22 while uniformly distributing stresses through the male screw 14 and female screw 24. The locking means 50 supplies the necessary clamping force to fully activate the wedge ramp 48 such that the crest 16 of the male screw 14 engages only the wedge ramp 48 and no other portion of the female screw 24 when in a locked condition. The locking means 50 in other words, eliminates the running clearance between threads when activated. Of course, the locking means 50 must be deactivated in order to permit readjustment of the stem 12 within the sleeve 26, i.e., to reestablish the running clearance between the screw threads.

The locking means 50 preferably comprises a jam nut 52 having a female screw formation 54 for threadably engaging the stem 12. The jam nut 52 is threaded along the male screw 14 in typical jam nut fashion against the adjustment collar 28 so as to place the portion of the stem 12 between the jam nut 52 and the adjustment collar 28 in tension. Such tensile forces cause the crest 16 of the male screw 14 to be drawn into forced contact with the wedge ramp 48 thereby activating the wedge ramp 48 to produce the unique and advantageous stress distribution equalizing features of the wedge ramp thread form. Whenever readjustment of the stem 12 axially relative to the sleeve 26 is desired, the jam nut 52 is threaded away from the adjustment collar 28 thereby relieving the tensile forces which urge the crest 16 of the male screw 14 into engagement with the wedge ramp 48 and thereby allowing the adjustment collar 28 to be rotated relative to the sleeve 26 with the stem 12 being displaced axially to the desired position.

Preferably, the female screw 54 of the jam nut 52 includes a helical thread crest 56 and thread root 58 with an interposed leading flank 60 facing toward the body fixation means 34 and a trailing flank 62 facing away from the body fixation means 34. Also, preferably, the female screw thread formation 54 of the jam nut 52 includes a wedge ramp 64 similar to the wedge ramp 48 described above. However, the wedge ramp 64 of the jam nut 52 is positioned across the root 58 and angles gradually and outwardly from the trailing flank 62 toward the leading flank 60. In other words, the wedge ramp 64 of the jam nut 52 is angled in the opposite direction of the wedge ramp 48 of the adjustment collar 28. Therefore, as the male screw 14 of the stem 12 is placed in tension when the jam nut 52 is brought to bear against the adjustment collar 28, the crest 16 of the male screw 14 will be drawn in proper fashion along the wedge ramp 64 of the jam nut 52, thereby evenly distributing the stresses through the jam nut 52 and the male screw 14 in the jam nut 52 area.

Although the preferred embodiment of the locking means 50 has been described with reference to the jam nut 52, it will be readily appreciated by those skilled in the art that other mechanical and/or electrical devices can be employed to simply maintain the crest 16 of the male screw 14 in pressed engagement with the wedge ramp 48 of the adjustment collar 28 to uniformly distribute stresses through the stem 12 and the adjustment collar 28. For example, a spring biasing mechanism applying a biasing force against the stem 12 would provide a similar and predictable response. Alternatively, a simple camming mechanism operative between the stem 12 and the adjustment collar 28 may be employed to forcibly maintain the crest 16 of the male screw 14 in pressed contact with the wedge ramp 48 when locking the stem 12 in an axially adjusted position.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. An adjustable length prosthetic implant for attaching to a bone, said implant comprising: an axially extending stem including a male screw having a helical thread crest; stem fixation means having an end portion shaped, sized and configured to extend into bone for mounting the stem to the bone; an implant body axially receiving the stem and including a female screw threadably engaging the male screw, the female screw having a helical wedge ramp for engaging the thread crest of the male screw; body fixation means for mounting the implant body at a location spaced from the stem fixation means; and locking means reactive between the implant body and the stem for forcibly maintaining the thread crest in pressed contact with the wedge ramp to lock the stem in an axially adjusted position relative to the implant body while uniformly distributing stresses through the male screw and the female screw.

2. A prosthesis as set forth in claim 1 wherein the implant body includes a tubular sleeve and an adjustment collar rotatably connected to the sleeve.

3. A prosthesis as set forth in claim 2 wherein the female screw is disposed in the adjustment collar.

4. An implant as set forth in claim 3 wherein the female screw includes a helical thread crest and a thread root with an interposed leading flank facing toward the body fixation means and a trailing flank facing away from the body fixation means, the wedge ramp positioned across the thread root and angling gradually and outwardly from the leading flank toward the trailing flank.

5. An implant as set forth in claim 4 wherein the locking means comprises a jam nut having a female screw for threadably engaging the stem.

6. An implant as set forth in claim 5 wherein the female screw of the jam nut includes a helical thread crest and a thread root with an interposed leading flank facing toward the body fixation means and a trailing flank facing away from the body fixation means, and a wedge ramp positioned across the thread root of the jam nut and angling gradually and outwardly from the trailing flank toward the leading flank of the jam nut.

7. An implant as set forth in claim 1 wherein the end portion of the stem fixation means becomes gradually slenderer toward the outer extremity thereof.

* * * * *